US005730989A

United States Patent [19]
Wright

[11] Patent Number: 5,730,989
[45] Date of Patent: Mar. 24, 1998

[54] ORAL VACCINE AGAINST GRAM NEGATIVE BACTERIAL INFECTION

[75] Inventor: D. Craig Wright, Gaithersburg, Md.

[73] Assignee: Novavax, Inc., Columbia, Md.

[21] Appl. No.: 482,552

[22] Filed: Jun. 7, 1995

Related U.S. Application Data

[63] Continuation-in-part of Ser. No. 389,637, Feb. 16, 1995, abandoned.

[51] Int. Cl.$^6$ .................. A61K 39/08; A61K 39/112; A61K 9/127
[52] U.S. Cl. .................. 424/241.1; 424/258.1; 424/255.1; 424/261.1; 424/249.1; 424/197.11; 424/450
[58] Field of Search .................. 424/249.1, 417, 424/420, 450, 184, 241, 251.1, 261.1, 184.1, 258.1, 197.11, 812

[56] References Cited

U.S. PATENT DOCUMENTS

| | | | |
|---|---|---|---|
| 4,235,871 | 11/1980 | Papahadjopoulos | 424/19 |
| 5,009,819 | 4/1991 | Popescu et al. | 264/4.1 |

OTHER PUBLICATIONS

Gregoriadis, G. (1990) "Immunological adjuvants: a role for liposomes" *Immunology Today* 11:89–97.
Ostro, M.J. (1987) "Liposomes" *Scientific American* 256(1):102–111.
Caprioli, A. et al. "Hemolytic–Uremic Syndrome and Vero Cytotoxin-Producing"*Escherichia coli* Infection in Italy'*Infectious Diseases* 166:154–158 (Jul. 1992).
Chart, H. et al. "Antibodies to *Escherichia coli* 0157 in patients with haemorrhagic colitis and haemolytic uraemic syndrome"*J. Clin. Pathol.* 42:973–976 (1989).
Chart, H et al. "Serological identification of *Escherichia coli* 0157:H7 infection in haemolyitc uraemic syndrome" *The Lancet* 337:138–40 (19 Jan. 1991).
Cross, A.S. et al. "Use of monoclonal antibody combinations in the prevention of bacteremia caused by *Escherichia coli*" *Serodiagnosis and Immunotherapy in Infectious Disease* 2:127–136 (1988).
Doyle, M.P. and J.L. Schoeni "Isolation of *Escherichia coli* 0157:H7 from Retail Fresh Meats and Poultry" *Applied and Environmental Microbiology* 53(1):2394–2396 (Oct. 1987).
Edelman, R. et al. "Summary of the International Symposium and Workshop on Infections Due to Verocytotoxin (Shiga–Like Toxin)–Producing *Escherichia coli*" *J. Infectious Diseases* 157(5):1102–1104 (May 1988).
Kaufman, B.M. et al. "Monoclonal Antibodies Reactive with K1–Encapsulated *Escherichia coli* Lipopolysaccharide are Opsonic and Protect Mice against Lethal Challenge" *Infection and Immunity* 52(2):617–619 (May 1986).
Kim, K.S. et al. "Functional Activities of Monoclonal Antibodies to the O Side Chain of *Escherichia coli* Lipopolysaccharides in Vitro and in Vivo" *Infectious Diseases* 157(1):47–53 (Jan. 1988).

Konowalchuk, J. et al. "Vero Response to a Cytotoxin of *Escherichia coli*" *Infection and Immunity* 18(3);775–779 (Dec. 1977).
Lopez, E.L. et al. "Evidence of infection with organisms producing Shiga–like toxins in household contacts of children with the hemolytic uremic syndrome" *Pediatric Infectious Disease J.* 10(1):20–24 (1991).
March, S.B. and S. Ratnam "Latex Agglutination Test for Detection of *Escherichia coli* Serotype 0157" *J. Clinical Microbiology* 27(7):1675–1677 (Jul. 1989).
March, S.B. and S. Ratnam "Sorbitol–MacConkey Medium for Detection of *Escherichia coli* 0157:H7 Associated with Hemorrhagic Colitis" *J. Clinical Microbiology* 23(5):869–872 (May 1986).
Ogasawara, T. et al. "Inhibition of protein synthesis by Vero toxin (VT2 or Shiga–like toxin II) produced by *Escherichia coli* 0157:H7 at the level of elongation factor 1–dependent aminoacyl–tRNA binding to ribosomes" *Microbial Pathogenesis* 4:127–135 (1988).
Pai, C.H. et al. "Sporadic Cases of Hemorrhagic Colitis Associated with *Escherichia coli* 0157:H7" *Annals of Internal Medicine* 101(6):738–742 (Dec. 1984).
Remis, R.S. et al. "Sporadic Cases of hemorrhagic Colitis Associated with *Escherichia coli* 0157:H7" *Annals of Internal Medicine* 101(5):624–626 (Nov. 1984).
Riley, L.W. "The Epidemiologic, Clinical, and Microbiologic Features of Hemorrhagic Colitis" *Ann. Rev. Microbiol.* 41:383–407 (1987).
Sadoff, J.C. et al. "Characterization of Mouse Monoclonal Antibodies Directed against *pseudomonas aeruginosa* Lipopolysaccharides" *Antibiot. Chemother.* 36:134–146 (1985).
Scotland, S.M. et al. "Two Distinct Toxins Active On Vero Cells From Escherichia Coli 0157" *The Lancet* ii:885–886 (19 Oct. 1985).
Varanelli, C. et al. "Non–Phospholipid Vesicles as Experimental Immunological Adjuvants" in *Liposome Technology*, 2nd Ed., vol. I: Liposome Preparation and Related Techniques, G. Gregoriadis (ed.) (Ann Arbor, MI: CRC Press, Inc., 1993) Chp. 17, 253–264.
Wallach, D.F.H. and R. Mathur "Non–Phospholipid Liposomes: Principles and Bulk Applications" in *Liposome Technology*, 2nd Ed., vol. I: Liposome Preparation and Related Techniques, G. Gregoriadis (ed.) (Ann Arbor, MI: CRC Press, Inc., 1993) Chp. 16, 241–252.

(List continued on next page.)

*Primary Examiner*—Hazel F. Siderry
*Attorney, Agent, or Firm*—Lahive & Cockfield, LLP

[57] ABSTRACT

The present invention concerns an oral preparation useful as an immunizing agent or vaccine against gram negative bacterial infection. This oral preparation can also be used as a treatment for those infected with gam negative bacteria. The preparations can be used against any gram negative bacterial infection, including *Escherichia coli*, *Shigella flexneri* 2a, and *Salmonella enteriditis*.

26 Claims, 5 Drawing Sheets

OTHER PUBLICATIONS

Wallach, D.F.H. and J.R. Philippot "New Type of Lipid Vesicle: Novasome™" in *Liposome Technology*, 2nd Ed., vol. I: Liposome Preparation and Related Techniques, G. Gregoriadis (ed.) (Ann Arbor, MI: CRC Press, Inc., 1993) Chp. 9, 142–156.

McQueen et al Gastroentenology 104:A742, 1993 Abstract.

Bergarmann et al Rev Infect Dis:10:939–950 1989.

Varanelli et al, Liposmoe Preparation & Related Techiques, Chapter 17 pp. 253–264, 1993.

Bergmann, K. and Waldman, R., "Stimulation of Secretory Antibody Following Oral Administration of Antigen, " *Reviews of Infectious Diseases*, vol. 10, No. 5, 939–950 (1988).

ORAL VACCINE AGAINST GRAM NEGATIVE BACTERIAL INFECTION

REFERENCE TO RELATED APPLICATIONS

This application is a continuation-in-part of 08/389,637, filed Feb. 16, 1995, now abandoned entitled "Gram Negative Bacterial Infection Vaccine", the contents of which are incorporated herein by reference.

BACKGROUND OF THE INVENTION

The present invention relates to oral vaccines. More particularly, the present invention concerns an oral vaccine, and methods for its use, for preventing and treating gram negative bacterial infection, e.g., *E. coli* infection. The vaccine uses a masking agent which disguises the fecal-like smell of the bacteria and allows oral use. The preferred masking agent also appears to provide adjuvant action.

Gram negative bacteria produce lipopolysaccharides as part of their cell walls. These lipopolysaccharides, which are designated as "smooth" or "rough" depending on their folding and other surface characteristics, have several regions, such as the O-side O-side chain in the smooth isolates. The O-side chains of the various smooth lipopoysaccharides can act as epitopes for antibody production. While some work has been carded out attempting to isolate and purify these lipopolysaccharides as antigens for immunization purpose, this has not been very successful.

In 1977, Knowalchuk identified *Escherichia coli* isolates which produced a cytotoxin for Vero cells. Patients subsequently found to be infected with verocytotoxin-producing enterohemorrhagic *E. coli* (EHEC) strains (0157:H7, 026 or 0111) developed one of the following: an asymptomatic infection with toxin in the stool, diarrhea, or hemorrhagic colitis. *E. coli* 0157:H7 was the first EHEC strain identified in humans and remains the most common infectious cause of bloody diarrhea and hemorrhagic colitis in humans. Fifteen to thirty-seven per cent of patients presenting with bloody diarrhea are infected with *E. coli* 0157:H7. *E. coli* 0157:H7 is a gram negative sorbitol non-fermenter and can be identified in stool specimens from patients by plating stool on MacConkey media containing sorbitol rather than lactose. The definitive identification of the serotype is accomplished by utilization of a latex agglutination assay.

*E. coli* 0157:H7 outbreaks have been associated with inadequately cooked hamburger, cold meat, non-chlorinated drinking water, and close contact with colonized or infected persons in institutional settings (i.e., mental hospitals, nursing homes or daycare). Beef and dairy cattle, pigs, lambs and poultry may all be environmental reservoirs for verocytotoxin-producing enterohemorrhagic *E. coli*. A percentage of symptomatic *E. coli* 0157:H7-infected children and adults may subsequently develop Hemolytic-Uremic Syndrome (HUS) or Thrombotic Thrombocytopenic Purpura (TTP). The development of HUS or TTP is felt to be secondary to the production of Shiga-like verocytotoxins (SLT-1 and SLT-2) by EHEC. Verocytotoxins produced by EHEC strains inhibit protein synthesis at the level of elongation factor 1-dependent aminoacyl-tRNA binding to ribosomes.

Those patients with *E. coli* infections that develop HUS or hemorrhagic colitis have been shown by enzyme-linked immunosorbent assay (ELISA) and/or western blot to generate a convalescent serum antibody to lipopolysaccharide in 64–73% of patients.

Some earlier work has shown that murine monoclonal antibodies directed against the O-side chain epitopes of lipopolysaccharides from *Escherichia coli* and *Pseudomonas aeruginosa* serotypes are protective against gram negative infection when given i.p. in murine and rat sepsis models. See, e.g., Kaufman et al, "Monoclonal antibodies reactive with K-1 encapsulated *Escherichia coli* lipopolysaccharide are opsonic and protect mice against lethal challenge," Inf. and Imm. 52 (2):617–619 (1986); and Kim et al., "Functional activities of monoclonal antibodies to the O side chain of *Escherichia coli* lipopolysaccharides in vitro and in vivo," J. Infectious Disease 2:47–53(1988). However, no one has determined whether antibodies to O-side chain specific epitopes of *E. coli* 0157:H7, or any other EHEC, might be generated by oral vaccination with an inactivated *E. coli* 0157:H7 (or similar gram negative bacteria such as *Shigella flexneri* or *Salmonella enteriditis*) vaccine. One bar to administration of an oral vaccine has been the unpleasant, fecal-like smell associated with these bacteria.

Accordingly, it is an object of the invention to provide an oral vaccine to produce antibodies to O-side chain epitopes of lipopolysaccharides of gram negative bacteria, particularly against *E. coli*, *S. flexneri*, and *S. enteriditis*.

An additional object of the invention is to provide an oral vaccine against gram negative bacterial infection in which the fecal smell associated with the bacteria has been masked so there is a pleasing smell.

Another object of the invention is to provide oral vaccines against gram negative bacterial infection stable at -20° C. and 4° C.

A further object of the invention is to provide a method of generating a serum antibody response to *E. coli*, *S. flexneri*, or *S. enteriditis* infection in vivo.

These and other objects and features of the invention will be apparent from the detailed description and the claims.

SUMMARY OF THE INVENTION

The present invention features an oral preparation for inoculation against gram negative bacteria, a method of preventing gram negative bacterial infection in vivo and a method of minimizing the effects of gram negative bacterial infection. The invention is particularly effective against the gram negative bacteria *E. coli*, *S. flexneri*, and *S. enteriditis*. The invention uses a combination product containing inactivated gram negative bacteria which contain the lipopolysaccharide antigen ("LPS"), and a masking agent. The masking agent is important because the gram negative bacteria such as *E. coli* still retain a fecal matter-like smell even after inactivation and/or lyophilization.

The basic preparation of the invention is an oral vaccine or medicament which provides protection against gram negative bacterial infection. This oral preparation includes the whole gram negative bacteria, in inactivated form, and a lipid vesicle-encapsulated masking agent. The preferred lipid vesicles for use in the invention are non-phospholipid, paucilamellar lipid vesicles having 2–8 lipid bilayers surrounding an amorphous central cavity. The preferred masking agent is a fragrance or flavoring encapsulated in the amorphous cavity of the lipid vesicles, most preferably in the form of a water-immiscible material which substantially fills the amorphous central cavity. Particularly preferred materials are the volatile oils such as cherry or peppermint oil. While the invention could be used to prevent any gram negative bacterial infection, verocytotoxin-producing enterohemorrhagic *E. coli* cells, *S. flexneri* cells, and *S. enteriditis* were selected. However, the method would also be effective using other gram negative bacteria, including bacteria of the families Spirosomaceae, Pseudomonadaceae, Azotobacteraceae, Rhizobiaceae, Methylococcaceae, Halobacteriaceae, Legionallaceae, Neisseriaceae, Vibrionaceae, Pasteurellaceae, Bacteroidaceae, and Enterobacteriaceae, particularly the genera Escherichia, Shigella, Salmonella, Citrobacter, Klebsiella, Enterobacter, Erwinia, Serratia, Hafnia, Edwardsiella, Proteus, Providencia, Morganella and Yersinia. Other genera include Aquaspirillum, Spirillum, Azospirillum, Oceanospirillum, Campylobacter, Helicobacter, Bdellovibrio, VampirovibrHelicobacter, Bdellovibrio, Vampirovibrio, and Gardinella. Whatever gram negative bacteria is used, the cells are inactivated using a standard method such as heat or formalin inactivation. The cells can be lyophilized and reconstituted with a reconstituting solution before use or they can be used immediately as is. If they are not lyophilized, the activity can deteriorate rapidly but if they are lyophilized and reconstituted, the lipid vesicle encapsulated masking agent can be used as the reconstituting solution.

The methods of the invention can be used to provide protection against gram negative infection, e.g., acting as a vaccine. An effective amount of the oral gram negative bacterial preparation is used to generate antibodies in vivo. The preferred antigens for generating the antibodies are the O-side chain epitopes of the lipopolysaccharides on the surfaces of strains of *E. coli* 0157:H7, *S. flexneri* 2a, and *S. enteriditis* bacteria. Since other gram negative bacteria have similar O-side chains on their lipopolysaccharides, similar procedures can be used for such other bacteria, as is known in the art. The bacteria are grown and isolated using standard microbiological methods and inactivated by heat or formalin. The resulting inactivated cells can be lyophilized using standard techniques and reconstituted. The oral product described previously is the preferred agent for providing protection in the form of a vaccine or for use in prevention of infection by generating antibodies to help minimize the effects of the infection.

Further advantages and details of the invention will be apparent from the detailed description and the claims.

BRIEF DESCRIPTION OF THE DRAWING

FIG. 1 shows murine IgM levels at day 58 after vaccination with *E. coli* 0157:H7 vaccine;

FIG. 2 shows murine IgG levels at day 58 after vaccination *E. coli* 0157:H7 vaccine;

FIG. 3 shows antibody tilers after a 7.5 mg dose of the *E. coli* 0157:H7 vaccine;

FIG. 4 shows antibody titers after a 1.875 mg dose of the *E. coli* 0157:H7 vaccine;

FIG. 5 shows antibody titers after a 2.618 mg dose of the *S. flexneri* 2a vaccine;

FIG. 6 shows antibody titers after a 10.47 mg dose of the *S. flexneri* 2a vaccine;

FIG. 7 shows antibody titer after a 3.937 mg dose of the *S. enteriditis* vaccine; and FIG. 8 shows antibody tilers after a 15.89 mg dose of the *S. enteriditis* vaccine.

DETAILED DESCRIPTION OF THE INVENTION

The present invention provides an oral preparation useful in vaccination against gram negative bacterial infection and method of its use. The same general preparation can also be used to treat gram negative bacterial infection by increasing the in vivo antibody response.

The basic process for producing the oral preparation of the invention commences with growth and harvest of the bacteria, inactivation, preferably but not exclusively with formaldehyde, and lyophilization of the whole cells. This process appears to maintain the antigenic integrity of the bacteria. Because of the feculent nature of the cells, the preferred diluent contains an aromatic oil, preferably a peppermint oil or a cherry-flavored oil, encapsulated in a non-phospholipid liposome (Novasome®) to enhance the palatability of the vaccine. These flavored Novasomes are composed of glycerol monostearate, soya sterols, soybean oil, cherry or peppermint oil, polysorbate 60, oleic acid, and water for injection. Details for preparation of lipid vesicles containing oil are disclosed in U.S. Pat. No. 4,911,928, the disclosure of which is incorporated herein by reference. However, other materials constituting the lipid vesicles, and other production methods, could be used so long as the flavor masking provision is met. An additional advantage of using the lipid vesicles described herein is that these vesicles appear to provide adjuvant activity in addition to their flavor masking capability. While such adjuvant activity is not necessary for practice of the invention, it may raise antibody titers, as described in U.S. Ser. No. 08/201,346, entitled "Vaccines Containing Paucilamellar Lipid Vesicles as Immunological Adjuvants", incorporated herein by reference.

The following example shows a lyophilized, formalin-inactivated *E. coli* 0157:H7 oral vaccine, reconstituted with cherry-flavored lipid vesicles in water for injection, which has been tested in animal models for both safety and immunogenicity. The vaccine is safe and immunogenic in mice and rats using a two-dose gavage regimen.

EXAMPLE I

This example illustrates the steps in preparing an oral vaccine of the invention, as well as tests for its safety. The *E. coli* 0157:H7 vaccine described herein is a sterile, formalin-inactivated whole bacteria, lyophilized product in a single-use vial containing 300 mg bacterial protein in phosphate-buffered saline, pH 7.5. The vaccine is stored at −20° C. until reconstitution with 10 mL of the Novasome-WFI [Water for Invention] diluent. The reconstituted vaccine should be administered within one hour.

The Novasome-WFI diluent is a paucilamellar, non-phospholipid liposome containing cherry-flavored oil to enhance the palatability of the *E. coli* 0157:H7 vaccine. This Novasome preparation is composed of glycerol monostearate (7.9%), soya sterols (2.2%), soybean oil (9.2%), cherry oil (4.5%), polysorbate 60 (2.1%), oleic acid (0.1%) and water for injection (74%). After production of the Novasome lipid vesicles, they are diluted with WFI in a ratio of Novasomes:WFI of 1:32 (v/v). The final percentage of water in the Novasome-WFI diluent is 99.2%. The resultant Novasome-WFI diluent is a sterile Novasome suspension in water for injection in a single use vial. The Novasome-WFI diluent is stored at room temperature. Ten milliliters of the Novasome-WFI diluent are utilized to reconstitute each bottle of the *E. coli* 0157:H7 vaccine.

The following steps are followed to produce the 0157:H7 vaccine.

Preparation of NOVASOME-WFI Diluent Vehicle

Step 1. Preparation of Lipid Oil Phase

The lipid phase consisted of:

| Glycerol Monostearate | 13.72 g |
|---|---|
| Polysorbate 60 (Tween 60) | 3.64 g |
| Generol 122 (Refined Soya Sterols) | 3.84 g |
| Oleic Acid | 240 μl |
| Cherry Oil | 8.0 g |
| Soybean Oil | 16.0 g |

All raw materials were added to a depyrogenated vessel which was then heated on a heating plate with agitation until all materials were melted. The lipid solution was then transferred to a sterile 50 mL conical centrifuge tube which was placed in an 85° C. circulating water bath for one hour.

Step 2. Preparation of Diluent

The diluent phase consisted of:

3.7 mL sterile water for injection for each 5 mL of Novasome preparation.

For each preparation, the sterile water for injection was drawn up in a 5 cc syringe which was placed in an incubator and heated to 65° C.

Step 3. Preparation of Mixing Instrument

A syringe mixing machine using 5 cc syringes was set for a lipid/oil to diluent ratio of 1.3:3.7. The speed controlling the force of pressure for mixing was adjusted to 70. This instrument is described in U.S. Pat. No. 4,895,452, the disclosure of which is incorporated herein by reference.

Step 4. Preparation of Novasome Lipid Vesicles

The heated lipid was drawn into a 5 cc LuerLok syringe and connected to the diluent syringe by way of a two-way stainless steel connector.

The syringes were then positioned into the Teflon mixing block and placed on the mixing machine. The solutions in the syringes were allowed to mix by pushing the liquids back and forth from one syringe to the other under pressure for 10 strokes at room temperature and then rapidly cooled using $CO_2$ for 90 strokes.

Several 5 cc Novasome lipid vesicle preparations were combined into a single solution in a depyrogenated vessel. Samples of the final pooled Novasome preparation were taken for USP sterility testing, endotoxin testing, pH determination, stability testing, and sub-micron particle sizing. More particularly, USP Sterility testing was performed on a 1.0 mL sample of the pooled Novasome preparation. No bacterial growth was observed in the liquid medium.

Step 5. Dilution of Novasomes 4,850 mL of sterile water for injection was filtered through a 0.2 μm filtering unit into a depyrogenated vessel containing a stir bar. 150 mL of pooled Novasome preparations was aseptically added to the diluent. The suspension was placed on a stir plate and allowed to mix for 24 hours. Three 5 L bottles of Novasome-WFI diluent were prepared. Samples were taken from each 5 L Novasome-WFI diluent bottle for USP sterility testing, endotoxin testing, and sub-micron particle sizing.

A 10 μL sample of the vaccine was plated onto TSA which was incubated for 48 hours at 37° C. as a test for sterility of the larger batch of diluent. Again, there was no growth observed on the solid or liquid medium.

*E. coli* 0157:H7 Vaccine Manufacturing and Control Data Preparation of *E. Coli* 0157:H7 Active Substance Step 1. Seed Culture The *Escherichia coli* 0157:H7 active material was derived from the *Escherichia coli* strain 0175:H7 (ATCC 43894). The seed was stored in 15% Glycerol Trypticase Soy broth at −70° C. and identified prior to initiating the starter culture. Culture identification was established by incubating the culture overnight on Trypticase Soy Agar with 5% Sheep Blood and MacConkey's Agar. The culture showed a homogenous smooth colonial morphology and revealed only gram negative rods by gram stain. The API biochemical profile was consistent with *E. coli* 0157:H7.

Step 2. Starter Culture Tubes

One colony from the TSA II plate of the seed culture was used to inoculate each of two 15 mL tubes of Trypticase Soy Broth (BBL). The cultures were grown on a rotor for 2 hours at 37° C., after which a subculture was taken for identity check.

Step 3. Starter Culture Flask 12 mL from the Trypticase Soy Broth culture was used to inoculate a Fernbach flask containing 1 L of Lauria Broth medium. The culture was grown on an incubator shaker at 150 rpm 37° C. for 3.5 hours after which a subculture was taken for identity check. The culture was incubated overnight on Trypticase Soy Agar with 5% Sheep Blood and MacConkey's Agar. The culture showed a homogenous smooth colonial morphology and revealed only gram negative rods by gram stain. The API biochemical profile was consistent with *E. coli* 0157:H7.

Step 4. Preparation of Growth and Fermentation Medium

Lauria Broth medium (pH 7.0) was used for the starter culture flask, as well as the fermentation process. The medium consisted of:

| | |
|---|---|
| Tryptone | 20 g/L |
| Yeast Extract | 10 g/L |
| Sodium chloride | 10 g/L |

The starter flask medium was sterilized in a steam autoclave for 30 minutes at a temperature setting of 121° C. The fermentation medium was sterilized in the fermentor at a temperature setting of 121° C. for 30 minutes. Samples of both media were taken for sterility testing prior to initiating the starter culture or the fermentation.

Step 5. Fermentation

Deionized water was added to a clean batch vessel. The ingredients for Lauria Broth medium were added with sufficient agitation for mixing and sufficient additional deionized water was then added to obtain 40 L. The solution was mixed, pumped into a 50 L B. Braun Fermento (Model Biostat U-50) and chased with sufficient deionized water to achieve a 50 L batch volume. The unit was sealed and the sterilization cycle started. 4 L of a 40 g/L dextrose solution was prepared and sterilized using a 0.2 µm membrane filter. The feed transfer line was aseptically connected to the fermentor and the dextrose feed was added. The incubation conditions (pH 7.0+/−0.02, temperature 37° C. +/−1° C., dissolved oxygen (D.O.) .+/−50%, air flow 80 +/−5 SLPM, agitation D.O. cascade, 300 rpm/min.) were automatically maintained. The pH was maintained with an automatic controller utilizing 20% glacial acetic acid and 4N sodium hydroxide. Foaming was automatically controlled utilizing PPG 2000 in an addition vessel. The 1 L starter culture was used to inoculate the fermentor.

The *E. coli* bacteria cells were allowed to ferment into log phase for 10 hours. Samples were obtained hourly for optical density (OD) measurement. When absorbance approached 1.0, dilutions were performed. Dextrose usage and foaming were monitored. Subcultures were taken from the starter flask and at the end of the fermentation run for identity testing of the isolate. Bacterial count (CFU/mL), pH, dextrose analysis and OD were performed on the final product.

Step 6. Harvest Cells were harvested using a Heraeus Varifuge (Model 20 RS) continuous centrifuge for 5.25 hours. Speed of the continuous rotor was controlled at 15,000 rpm and temperature was controlled to less than 25° C. Supernatant samples were analyzed periodically during centrifugation for optimization of centrifugation. 250 g of cell paste was then aseptically transferred to each of 5 1 L Nalgene centrifuge bottles for further processing. Centrifuge bottles were weighed prior to addition of cell paste and the weight was recorded.

Step 7. Formaldehyde Treatment of Cell Paste

Six liters of 1.5% formaldehyde solution were prepared using Phosphate Buffered Saline (PBS) (146 mM Na-10mM $PO_4$) diluent. Samples of PBS were taken for USP Sterility and endotoxin testing as well as pH determination. The 1.5% Formaldehyde PBS solution was added to each centrifuge bottle to achieve a weight of 1.035 g. The paste was resuspended by agitation after which centrifuge bottles were allowed to stir at 4° C. on a stir plate for 96 hours. Samples from each centrifuge bottle were taken at 24 and 96 hours and plated on TSA II plates for monitoring of viability.

After 96 hours, the formaldehyde inactivated paste was centrifuged for 4 hours at 4000 rpm 4° C. in a Beckman refrigerated centrifuge (Model J-6B). Supernatant was discarded and sufficient PBS was added to each bottle to achieve the initial weight. Paste was resuspended by agitation, after which bottles were centrifuged for 4 hours at 4000 rpm at 4° C. in a Beckman refrigerated centrifuge (Model J-6B). The supernatant from this centrifugation was discarded and the wash process was repeated. Samples of PBS were taken for USP Sterility and endotoxin testing (see IPC) as well as pH determination. There was no growth observed in the liquid medium. An endotoxin assay was also performed using the Limulus Lysate Assay (Cape Cod Associates). The endotoxin level was at an acceptable level of <0.03 EU/mL. As an additional check on the viability, a 10 μL sample of the product was taken at 24 and 96 hours after formalin inactivation and plated onto TSA II which was incubated for 48 hours at 37° C. There was no growth observed on the solid medium.

Step 8. Resuspension of Formaldehyde Inactivated Paste

The formaldehyde inactivated bacterial paste was resuspended by agitation in PBS at a concentration of 1 g/5mL of PBS. Samples were taken from each centrifuge bottle of the final product for USP sterility testing. USP Sterility testing was performed on a 1.0 mL sample of the resuspended formaldehyde inactivated paste. A 10 μL sample of the vaccine was also plated onto TSA which was incubated for 48 hours at 37° C. There was no growth observed on the solid or liquid medium.

Step 9. Lyophilization

The formaldehyde inactivated vaccine was aseptically filled into 50 mL vials using a Sepco filling machine with presterilized syringe and robing apparatus, with 10 mL of the paste placed in each vial. The product was frozen to −40° C. on the lyophilizer shelf. The lyophilization chamber was evacuated to 100 μm and the product remained at −20° C. for 16 hours. The temperature was then elevated to 0° C. for 7 hours, after which it was elevated to 25° C. for 14 hours. 40 samples were taken for USP Sterility testing and 10 samples were analyzed for residual moisture assay. The vaccine passed both tests. The lyophilized vaccine was stored at −20° C.

Murine Immunogenicity Study

Mice were divided into 4 groups of 10 mice each. All the mice in a group received the *E. coli* 0157:H7 vaccine reconstituted in cherry-flavored Novasome-WFI diluent at doses of 7.50, 1.875, 0.9375, and 0.1875 mg of protein, respectively. Vaccine doses were given on Day 0 and Day 30 and were administered by garage. The animals were prebled 4 days before receiving their first vaccine dose, and were test-bled on Days 14, 28, 44, and 58.

Two animals died during the course of the study: one in the 1.875 mg dose group died on Day 30, and one in the 0.9375 mg dose group died on Day 5.

Mouse sera were tested by ELISA for the presence of antibody to *E. coli* 0157:H7 LPS. Test sera were serially diluted in flat-bottomed ELISA plates previously coated with *E. coli* 0157:H7 LPS and blocked. After two hours of incubation at room temperature, the plates were washed and incubated with enzyme-labeled goat anti-mouse IgM or anti-mouse IgG second antibody for 1 hour. After further washing, the plates were developed with a colorigenic substrate, and read using an automated ELISA plate reader. Anti-LPS antibody titers were the reciprocal of the serum dilution producing an optical density (OD) reading 3× the OD reading of the homologous prebleed.

The IgG subclass response was determined by using enzyme-labeled second antibodies specific for mouse $IgG_1$, $IgG_{2a}$, $IgG_{2b}$, and $IgG_3$.

Sera showing high pre-bleed ELISA titers against *E. coli* 0157:H7 LPS were screened for antibody specificity by western blot. Purified *E. coli* 0157:H7 LPS was separated by polyacrylamide gel electrophoresis and electrophoretically transferred to nitrocellulose sheets, which were then blocked, cut into strips, and dried. For screening, strips were incubated with a 1:100 dilution of the test serum for 2–4 hours, washed, incubated with an enzyme-labeled second antibody, rewashed, and developed with a precipitating colorigenic substrate.

Figure 1:
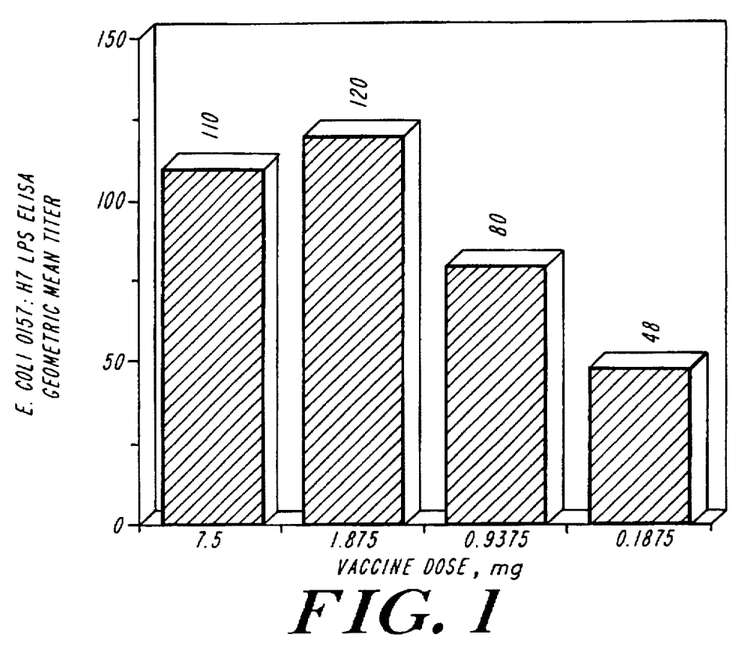
Figure 2:
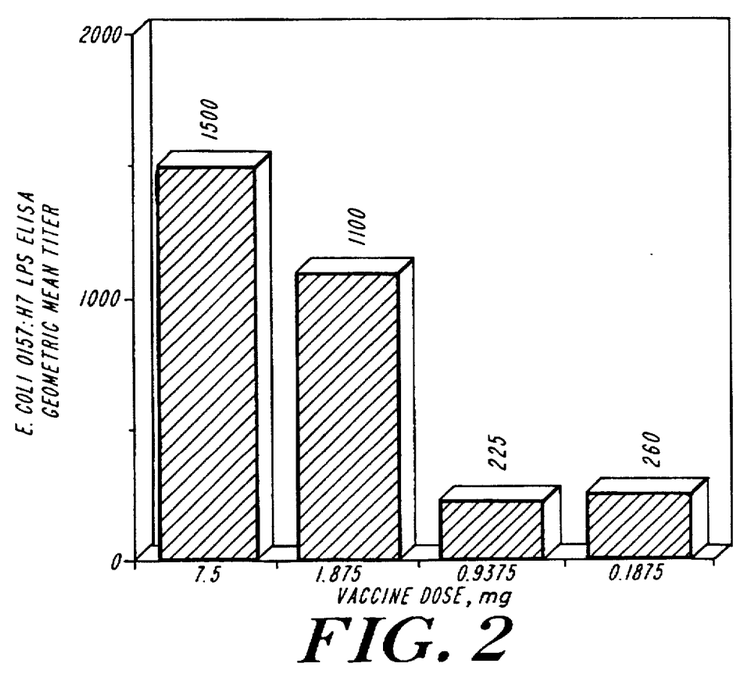

Both the LPS-specific IgM and IgG titers at Day 58 were dose-dependent. The two higher doses of vaccine produced IgM titers on Day 58 that were roughly equivalent (FIG. 1), as were the 58-day IgG titers at the same two doses (FIG. 2). In both cases, the titers resulting from the lower doses of vaccine were correspondingly lower. The 58-day IgG titers were approximately 10-fold higher than the IgM titers.

Figure 3:
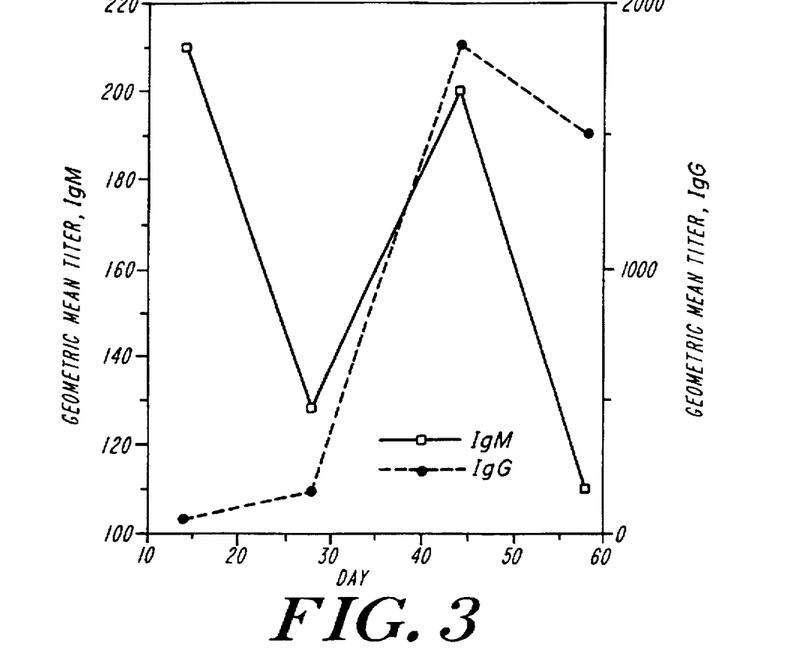
Figure 4:
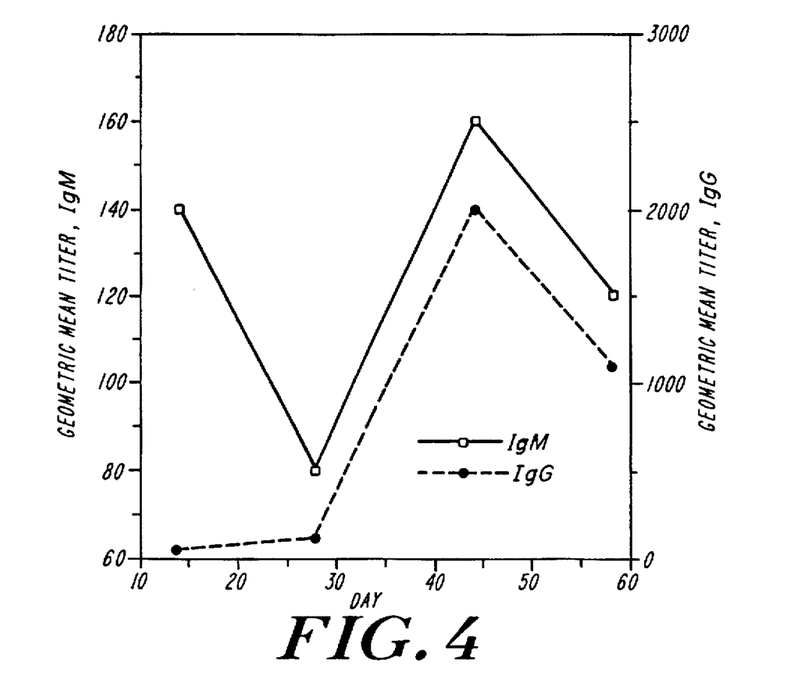

Significant IgM titers were obtained 14 days after the initial dose with the vaccine preparation at doses of 7.50 mg (FIG. 3) and 1.875 mg (FIG. 4). IgM displayed an anamnestic response after the second vaccine dose. IgG titers, which were low 28 days after the initial dose, rose dramatically after the second dose, and remained high at Day 58 (28 days after the second dose; FIGS. 3 and 4).

EXAMPLE II

This example illustrates a second oral vaccine of the invention. Like the *E. coli* preparation of Example I, this vaccine is also prepared using sterile formalin-inactivated whole bacteria. In this case, the bacteria is *Shigella flexneri* 2a. The vaccine, 419 mg bacterial protein in PBS at pH 7.15, is stored at −20° C. until reconstituted with 10 mL of the Novasome WFI diluent.

The diluent and the vaccine are prepared according to the procedures set forth in Example I.

Murine Immunogenicity Study

Mice were divided into four groups of 15 mice each. The mice in each group received the *S. flexneri* 2a vaccine reconstituted in cherry flavored Novasome diluent at doses of 10.47 mg, 2.618 mg, 1.309 mg, and 0.2618 mg of protein, respectively. Vaccine doses were given on Day 0 and Day 30, and were administered by garage. The animals were bled 4 days before receiving their first vaccine dose, and were test-bled on Days 14, 28, 44 and 58.

Sera showing high pre-bleed ELISA titers against *S. flexneri* LPS were screened for antibody specificity by western blot. Purified *S. flexneri* LPS was separated by polyacrylamide gel electrophoresis and electrophoretically transferred to nitrocellulose sheets, which were then blocked, cut into strips, and dried. For screening, strips were incubated with a 1:100 dilution of the test serum for 2–4 hours, washed, incubated with an enzyme-labeled second antibody, rewashed, and developed with a precipitating colorigenic substrate.

Figure 5:
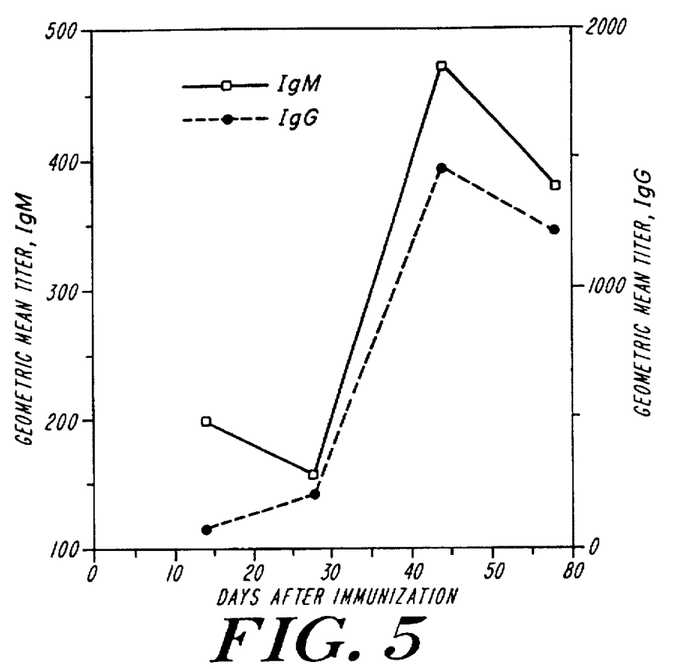
Figure 6:
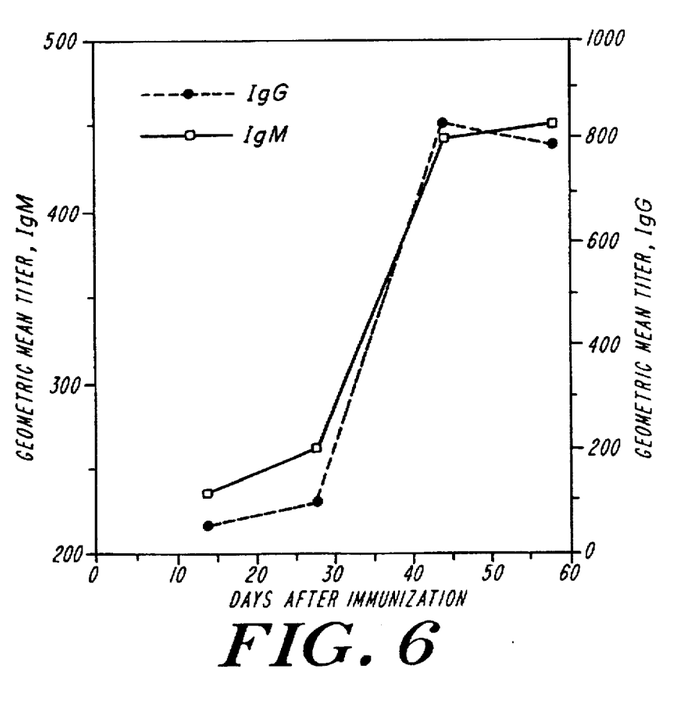
Figure 7:
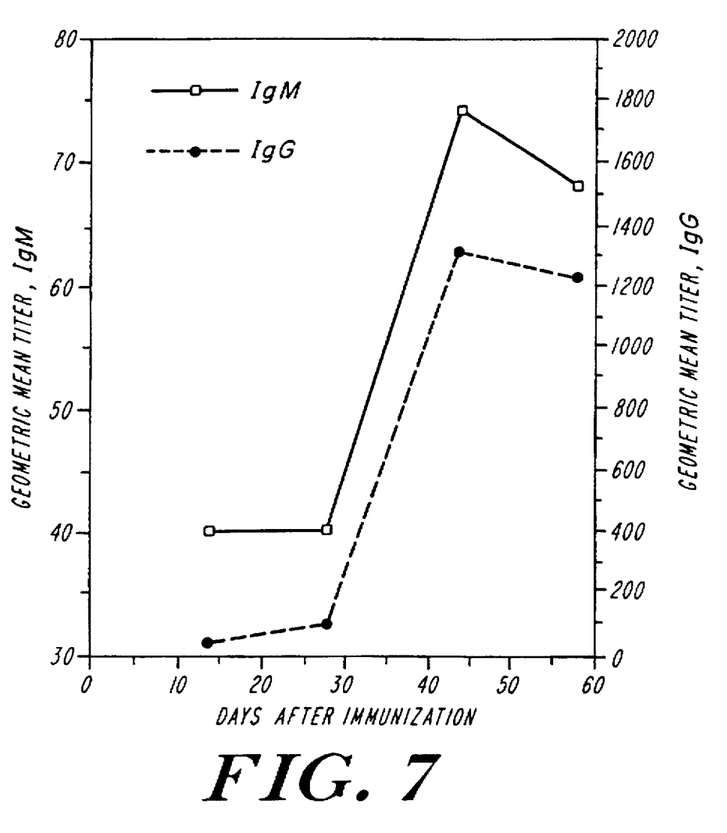
Figure 8:
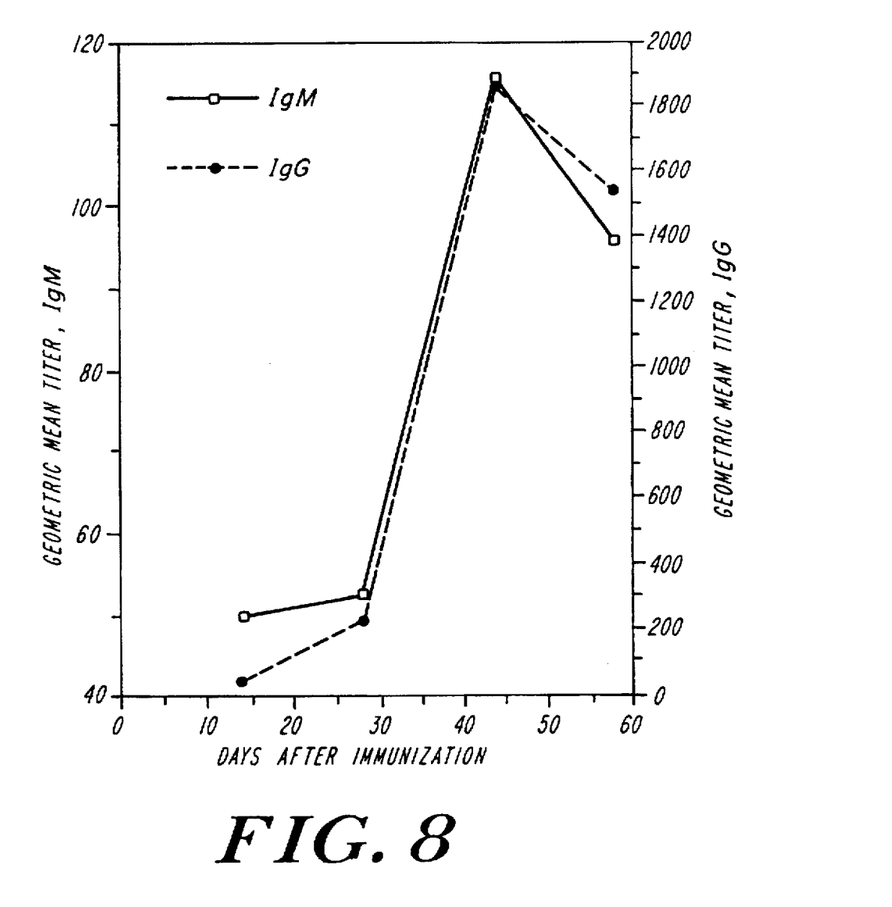

Both the LPS-specific IgM and IgG titers at Day 58 were dose-dependent. IgG and IgM titers rose dramatically after the second dose, and remained high at Day 58 (28 days after the second dose; FIGS. 5 and 6).

EXAMPLE III

This example illustrates a third oral vaccine of the invention. Like the *E. coli* preparation in Example I, this vaccine is also prepared using sterile formalin-inactivated whole bacteria. In this case, the bacteria is *Salmonella enteriditis*. The vaccine, 653 mg bacterial protein in PBS at pH 7.15, is stored at −20° C. until reconstituted with 10 mL of the Novasome WFI diluent.

The diluent and the vaccine are prepared according to the procedures set forth in Example I.

Murine Immunogenicity Study

Mice were divided into four groups of 15 mice each. The mice in each group received the *Salmonella enteriditis* vaccine reconstituted in cherry flavored Novasome diluent at doses of 15.89 mg, 3.973 mg, 1.986 mg, and 0.397 mg of protein respectively. Vaccine doses were given on Day 0 and Day 30, and were administered by garage. The animals were bled 3 days before receiving their first vaccine dose, and were test bled on Days 14, 28, 44, and 58.

Sera showing high pre-bleed ELISA titers against *S. enteriditis* LPS were screened for antibody specificity by western blot. Purified *S. enteriditis* LPS was separated by polyacrylamide gel electrophoresis and electrophoretically transferred to nitrocellulose sheets, which were then blocked, cut into strips, and dried. For screening, strips were incubated with a 1:100 dilution of the test serum for 2–4 hours, washed, incubated with an enzyme-labeled second antibody, rewashed, and developed with a precipitating colorigenic substrate.

Both the LPS-specific IgM and IgG titers at Day 58 were dose-dependent. IgG and IgM titers rose dramatically after the second dose, and remained high at Day 58 (28 days after the second dose; FIGS. 5 and 6).

From the foregoing, it is apparent that the orally administered, inactivated whole bacteria vaccines of the present invention are safe and immunogenic.

The foregoing description of the invention is meant to be only exemplary and is not intended to limit the scope of the invention. The invention is defined by the following claims.

What is claimed is:

1. An oral vaccine preparation for generating anti-LPS antibodies for treating gram negative infection, said oral vaccine preparation comprising inactivated gram negative bacteria and a lipid vesicle encapsulated flavor masking agent, said lipid vesicle comprising a paucilamellar lipid vesicle having 2–8 lipid bilayers surrounding an amorphous central cavity, and said paucilamellar lipid vesicle comprising a non-phospholipid material as a primary lipid in the bilayers.

2. The oral vaccine of claim 1 wherein said flavor masking agent comprises a fragrance encapsulated in said amorphous cavity of said lipid vesicle.

3. The oral vaccine of claim 2 wherein said fragrance comprises a water-immiscible material substantially filling said amorphous central cavity.

4. The oral vaccine of claim 3 wherein said fragrance comprises a flavored oil.

5. The oral vaccine of claim 1 wherein said gram negative bacteria are Enterobacteriaceae.

6. The oral vaccine of claim 5 wherein said gram negative bacteria is selected from the group consisting of Escherichia, Shigella, and Salmonella.

7. The oral vaccine of claim 6 wherein said gram negative bacteria comprises enterohemorrhagic *E. coli* bacteria.

8. The oral vaccine of claim 6 wherein said *E. coli* bacteria are selected from the group consisting of 0157:H7, 026 and 0111 bacteria.

9. The oral vaccine of claim 6 wherein said gram negative bacteria comprises *Shigella flexneri* 2a bacteria.

10. The oral vaccine of claim 6 wherein said gram negative bacteria comprises *Salmonella enteriditis* bacteria.

11. The oral vaccine of claim 1 wherein said gram negative bacteria are selected from the group consisting of formalin inactivated and heat inactivated cells.

12. The oral vaccine of claim 1 wherein said gram negative bacteria are lyophilized and reconstituted with a reconstituting solution before use.

13. The oral vaccine of claim 1 wherein said lipid vesicle encapsulated flavor masking agent comprises a reconstituting solution.

14. A method of providing treatment against gram negative bacterial infection comprising oral administration of an effective amount of an oral vaccine including as active components inactivated gram negative bacteria and a lipid vesicle encapsulated flavor masking agent, where said paucilamellar lipid vesicle comprises a paucilamellar lipid vesicle having 2–8 lipid bilayers surrounding an amorphous central cavity, and said paucilmellar lipid vesicles comprising non-phospholipid materials as a primary lipid in the bilayers.

15. The method of claim 14 wherein said flavor masking agent comprises a flavoring encapsulated in said amorphous cavity of said lipid vesicle.

16. The method of claim 15 wherein said flavoring comprises a water-immiscible material substantially filling said amorphous central cavity.

17. The method of claim 16 wherein said flavoring comprises a flavored oil.

18. The method of claim 14 wherein said gram negative bacteria are Enterobacteriaceae.

19. The method of claim 18 wherein said gram negative bacteria is selected from the group consisting of Escherichia, Shigella, and Salmonella.

20. The method of claim 19 wherein said gram negative bacteria comprises *E. coli*.

21. The method of claim 20 wherein said *E. coli* are selected from the group consisting of 0157:H7, 026 and 0111.

22. The method of claim 19 wherein said gram negative bacteria comprises *Shigella flexneri* 2a.

23. The method of claim 19 wherein said gram negative bacteria comprises *Salmonella enteriditis*.

24. The method of claim 14 wherein said gram negative bacteria are formalin inactivated.

25. The method of claim 14 wherein said gram negative bacteria are lyophilized and reconstituted with a reconstituting solution before use.

26. The method of claim 25 wherein said reconstituting solution comprises said lipid vesicle encapsulated flavor masking agent.

* * * * *